(12) United States Patent
Pacetti

(10) Patent No.: US 8,337,937 B2
(45) Date of Patent: *Dec. 25, 2012

(54) STENT SPIN COATING METHOD

(75) Inventor: Stephen D. Pacetti, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1237 days.

This patent is subject to a terminal disclaimer.

(21) Appl. No.: 12/134,477

(22) Filed: Jun. 6, 2008

(65) Prior Publication Data

US 2008/0234812 A1 Sep. 25, 2008

Related U.S. Application Data

(63) Continuation-in-part of application No. 10/262,161, filed on Sep. 30, 2002, now Pat. No. 7,404,979.

(51) Int. Cl.
*B05D 1/02* (2006.01)
*B05D 1/40* (2006.01)
*A61F 2/82* (2006.01)

(52) U.S. Cl. ......... 427/2.24; 427/240; 427/425; 118/52; 118/320; 118/323; 118/500

(58) Field of Classification Search .................. 427/2.24, 427/240, 425; 118/52, 500, 320, 323
See application file for complete search history.

(56) References Cited

U.S. PATENT DOCUMENTS

| | | | |
|---|---|---|---|
| 4,201,149 A | 5/1980 | Koester et al. | |
| 4,208,454 A | 6/1980 | Reed et al. | |
| 4,640,846 A | 2/1987 | Kuo | |
| 4,733,665 A | 3/1988 | Palmaz | |
| 4,800,882 A | 1/1989 | Gianturco | |
| 4,886,062 A | 12/1989 | Wiktor | |
| 4,977,901 A | 12/1990 | Ofstead | |
| 5,095,848 A | 3/1992 | Ikeno | |
| 5,112,457 A | 5/1992 | Marchant | |
| 5,264,246 A | 11/1993 | Ikeno | |
| 5,328,471 A | 7/1994 | Slepian | |
| 5,378,511 A | 1/1995 | Cardinali et al. | |
| 5,455,040 A | 10/1995 | Marchant | |
| 5,464,650 A | 11/1995 | Berg et al. | |
| 5,578,073 A | 11/1996 | Haimovich et al. | |
| 5,605,696 A | 2/1997 | Eury et al. | |
| 5,667,767 A | 9/1997 | Greff et al. | |
| 5,670,558 A | 9/1997 | Onishi et al. | |
| 5,700,286 A | 12/1997 | Tartaglia et al. | |
| 5,716,981 A | 2/1998 | Hunter et al. | |
| 5,824,049 A | 10/1998 | Ragheb et al. | |
| 5,830,178 A | 11/1998 | Jones et al. | |
| 5,837,313 A | 11/1998 | Ding et al. | |
| 5,851,508 A | 12/1998 | Greff et al. | |
| 5,858,746 A | 1/1999 | Hubbell et al. | |
| 5,865,814 A | 2/1999 | Tuch | |
| 5,873,904 A | 2/1999 | Ragheb et al. | |
| 5,971,954 A | 10/1999 | Conway et al. | |

(Continued)

FOREIGN PATENT DOCUMENTS

EP 0 665 023 8/1995

(Continued)

*Primary Examiner* — Kirsten Jolley

(74) *Attorney, Agent, or Firm* — Squire Sanders (US) LLP

(57) ABSTRACT

A method is disclosed for spin coating a stent. The method comprises conducting the following acts at the same time: applying a coating substance to the stent; rotating the stent about a first axis of rotation; and rotating the stent about a second axis of rotation.

12 Claims, 1 Drawing Sheet

U.S. PATENT DOCUMENTS

| | | | |
|---|---|---|---|
| 5,980,928 | A | 11/1999 | Terry |
| 5,980,972 | A | 11/1999 | Ding |
| 6,015,541 | A | 1/2000 | Greff et al. |
| 6,042,875 | A | 3/2000 | Ding et al. |
| 6,051,648 | A | 4/2000 | Rhee et al. |
| 6,056,993 | A | 5/2000 | Leidner et al. |
| 6,060,451 | A | 5/2000 | DiMaio et al. |
| 6,080,488 | A | 6/2000 | Hostettler et al. |
| 6,096,070 | A | 8/2000 | Ragheb et al. |
| 6,099,562 | A | 8/2000 | Ding et al. |
| 6,110,188 | A | 8/2000 | Narciso, Jr. |
| 6,113,629 | A | 9/2000 | Ken |
| 6,120,536 | A | 9/2000 | Ding et al. |
| 6,120,904 | A | 9/2000 | Hostettler et al. |
| 6,121,027 | A | 9/2000 | Clapper et al. |
| 6,129,761 | A | 10/2000 | Hubbell |
| 6,153,252 | A | 11/2000 | Hossainy et al. |
| 6,165,212 | A | 12/2000 | Dereume et al. |
| 6,165,267 | A | 12/2000 | Torczynski |
| 6,174,329 | B1 | 1/2001 | Callol et al. |
| 6,197,013 | B1 | 3/2001 | Reed et al. |
| 6,214,115 | B1 | 4/2001 | Taylor et al. |
| 6,235,340 | B1 | 5/2001 | Lee et al. |
| 6,261,320 | B1 | 7/2001 | Tam et al. |
| 6,287,249 | B1 | 9/2001 | Tam et al. |
| 4,733,665 | C1 | 1/2002 | Palmaz |
| 6,555,157 | B1 | 4/2003 | Hossainy |
| 6,562,136 | B1 | 5/2003 | Chappa et al. |
| 6,709,514 | B1 | 3/2004 | Hossainy |
| 6,730,349 | B2 | 5/2004 | Schwarz et al. |
| 7,192,484 | B2 | 3/2007 | Chappa et al. |
| 7,404,979 | B1 | 7/2008 | Pacetti |
| 8,042,486 | B2 | 10/2011 | Pacetti |
| 2003/0044514 | A1 | 3/2003 | Richard |
| 2003/0215564 | A1 | 11/2003 | Heller et al. |
| 2004/0047994 | A1 | 3/2004 | Becker et al. |
| 2004/0261698 | A1 | 12/2004 | Roorda et al. |

FOREIGN PATENT DOCUMENTS

| | | |
|---|---|---|
| EP | 0 970 711 | 1/2000 |
| WO | WO 00/12147 | 3/2000 |
| WO | WO 00/64506 | 11/2000 |
| WO | WO 01/01890 | 1/2001 |

STENT SPIN COATING METHOD

CROSS-REFERENCE

This is a continuation-in-part of application Ser. No. 10/262,161, filed on Sep. 30, 2002, now U.S. Pat. No. 7,404,979.

BACKGROUND

1. Field of the Invention

This invention relates to a method for spin coating implantable medical devices such as stents.

2. Description of the State of the Art

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress against the atherosclerotic plaque of the lesion to remodel the lumen wall. The balloon is then deflated to a smaller profile to allow the catheter to be withdrawn from the patient's vasculature.

A problem associated with the above procedure includes formation of intimal flaps or torn arterial linings which can collapse and occlude the conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of arterial lining, and to reduce the chance of the development of restenosis, a stent is implanted in the lumen to maintain the vascular patency.

Stents are used not only as a mechanical intervention but also as a vehicle for providing biological therapy. As a mechanical intervention, stents act as scaffoldings, functioning to physically hold open and, if desired, to expand the wall of the passageway. Typically, stents are capable of being compressed, so that they can be inserted through small vessels via catheters, and then expanded to a larger diameter once they are at the desired location. Examples in patent literature disclosing stents which have been applied in PTCA procedures include stents illustrated in U.S. Pat. No. 4,733,665 issued to Palmaz, U.S. Pat. No. 4,800,882 issued to Gianturco, and U.S. Pat. No. 4,886,062 issued to Wiktor.

Biological therapy can be achieved by medicating the stents. Medicated stents provide for the local administration of a therapeutic substance at the diseased site. In order to provide an efficacious concentration to the treated site, systemic administration of such medication often produces adverse or toxic side effects for the patient. Local delivery is a preferred method of treatment in that smaller total levels of medication are administered in comparison to systemic dosages, but are concentrated at a specific site. Local delivery thus produces fewer side effects and achieves more favorable results.

One proposed method for medicating stents involves the use of a polymeric carrier coated onto the surface of a stent. A solution which includes a solvent, a polymer dissolved in the solvent, and a therapeutic substance dispersed in the blend is applied to the stent. The solvent is allowed to evaporate, leaving on the stent surface a coating of the polymer and the therapeutic substance impregnated in the polymer.

One conventional technique of coating a stent is by spraying the stent with the coating composition. If the coating solvent is sufficiently volatile, the spray process can spray continuously, building up coating thickness. However, if the solvent evaporates more slowly than it is being applied, the resulting stent coating may have undesirable imperfections such as formation of "webbing" of the coating between the stent struts. One current solution to this problem is to spray coat in a pulsed mode, interleaving brief spray blasts with forced-air drying. Spray coating processes, therefore, can be lengthy and have a greater opportunity for coating variability due to the complexity of the process.

Accordingly, a stent coating process that is rapid, produces a uniform coating, and is highly reproducible is needed. The embodiments of the invention provide an apparatus for fabricating coatings for implantable devices, such as stents, and methods of coating the same.

SUMMARY

Briefly and in general terms, the present invention is directed to a method of coating a stent.

In aspects of the present invention, a method comprises conducting the following acts at the same time: applying a coating substance to the stent, rotating the stent about a first axis of rotation, and rotating the stent about a second axis of rotation, wherein the first axis of rotation is not parallel and not perpendicular to the second axis of rotation.

In other aspects, the first axis of rotation intersects a center of the mass of the stent and the second axis of rotation is along a longitudinal central axis of the stent.

In other aspects, the first axis of rotation intersects a part of the body of the stent and the second axis of rotation is along a longitudinal central axis of the stent.

In other aspects, the stent is positioned off-set, at a distance away from the first axis of rotation.

In other aspects, the first axis of rotation intersects the second axis of rotation at an angle. In aspects of the present invention, a method comprises conducting the following acts at the same time: applying a coating substance to the stent, rotating the stent about a first axis of rotation, and rotating the stent about a second axis of rotation, wherein the first axis of rotation intersects the second axis of rotation at an angle.

In other aspects, the first axis of rotation is perpendicular to the second axis of rotation.

In other aspects, the first axis of rotation intersects a center of the mass of the stent and the second axis of rotation is along a longitudinal central axis of the stent.

In other aspects, the first axis of rotation intersects a part of the body of the stent and the second axis of rotation is along a longitudinal central axis of the stent.

In other aspects, the first axis of rotation intersects a center of the mass of the stent, the second axis of rotation is along a longitudinal central axis of the stent, and the first axis of rotation is perpendicular to the second axis of rotation.

In other aspects, the stent is positioned off-set, at a distance away from the first axis of rotation.

In other aspects, the first axis of rotation is perpendicular to a longitudinal axis of the stent.

DETAILED DESCRIPTION

I. Apparatus

Figure 1:
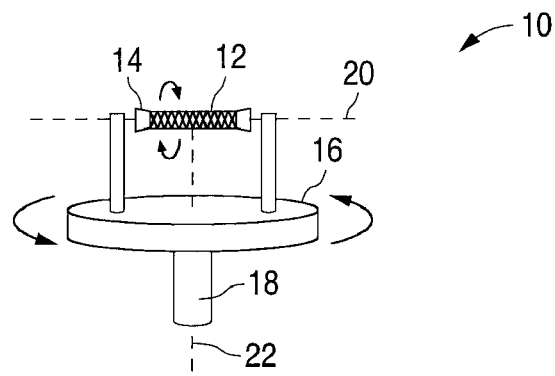
FIG. 1 illustrates one embodiment of the apparatus for coating implantable medical devices.

FIG. 1 illustrates one embodiment of a coating apparatus 10. The coating apparatus 10 includes a mandrel 14 on which a stent 12 can be securely positioned. The mandrel 14 is mounted above a round table 16 using mandrel arms attached to the table 16. The table 16 can be rotated about a shaft 18 using a motor (not shown). A longitudinal axis 20 of the stent can be substantially perpendicular to an axis of rotation 22 of the table 16. The axis of rotation 22 of table 16 can extend along the center of the table 16. The stent 12 can be positioned in such a way that the axis of rotation 22 intersects the center of mass of the stent 12. The mandrel 14 can be connected to a second motor (not shown) using suitable bearings and gears and rotated about the longitudinal axis 20. The table 16 can have a radius of between about 2 cm and about 20 cm, for example about 4 cm. The mandrel 14 is selected so as to accommodate stents of various sizes. For example, coronary stents having the length of between about 8 and about 38 mm, and peripheral stents having a length of about 76 mm can be used.

Figure 2:
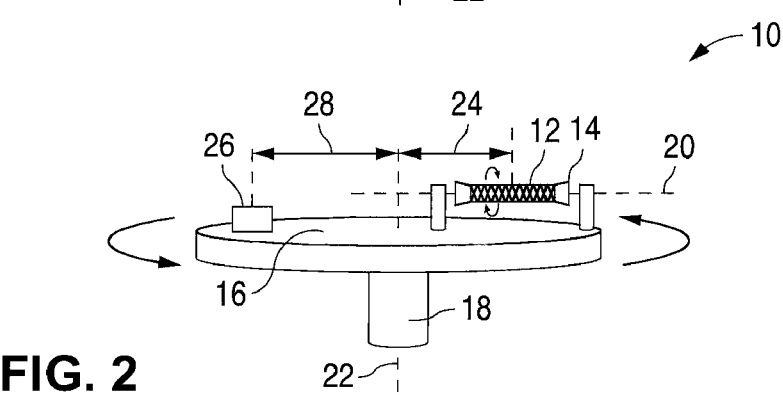
FIG. 2 illustrates another embodiment of the apparatus.

FIG. 2 illustrates another embodiment of the coating apparatus. The stent 12 is positioned offset from the axis of rotation 22. An offset distance 24 can be measured as the distance between the axis of rotation 22 and the composite center of mass for the stent 12. The offset distance 24 can be within a range of between about 0.1 cm and about 20 cm, for example about 15 cm. At least one counterweight 26 can be mounted on the table 16. Those having ordinary skill in the art can determine the appropriate mass and location of the counterweight 26. For example, the mass of the counterweight 26 can made be equivalent to the composite mass of the stent 12, the mandrel 14, and the mandrel arms. The counterweight radius 28 can be made equivalent to the offset distance 24. The counterweight radius 28 can be measured as the distance between the axis 22 and the center of mass of the counterweight 26.

As best illustrated by FIG. 2, although the stent 12 is in an offset position, the longitudinal axis of the stent 20 intersects the axis of rotation 22 at about a 90 degree angle. The longitudinal axis 20 of the stent 12 need not intersect the axis of rotation 22. The axis of rotation 22 remains perpendicular to a plane parallel to the surface of the table 16 and extending along the longitudinal axis 20 of the stent 12.

Figure 3:
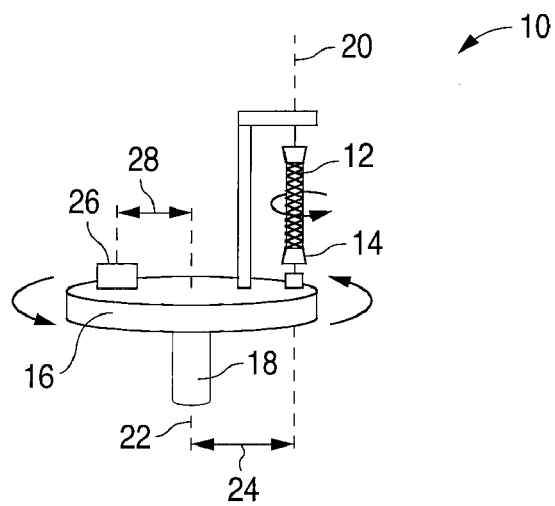
FIG. 3 illustrates another embodiment of the invention.

In yet another embodiment, as illustrated by FIG. 3, the longitudinal axis 20 of the stent 12 is parallel to the rotational axis 22. The mandrel 14 can be also optionally offset from the axis of rotation 22. If the stent 12 is positioned at the offset distance 24 away from the axis of rotation 22, the counterweight 26 should be used to balance the system. The mandrel 14 can also be rotated about the longitudinal axis 20 by a motor.

In some embodiments, the longitudinal axis 20 of the stent 12 can be non-parallel to the rotational axis 22. In some embodiments, the longitudinal axis 20 can be not parallel as well as not perpendicular, such that it is positioned at an angle to axis 22. The angle between 20 and 22 can be for example 60, 45, or 30 degrees.

II. Method

A coating system can be applied to the stent 12 by any suitable method known to those having ordinary skill in the art, such as, for example, by spraying, dip-coating, brushing or wiping. Preferably it is by spraying. The coating system can be applied before the stent 12 has been mounted onto the apparatus 10. Alternatively, the stent 12 can be coated after being mounted onto the apparatus 10. The coating can be applied before the rotation of the stent 12 on the table 16 and along the axis 20 of the stent 12 such that the application of the coating (e.g., by spray) is completely terminated before the rotation of the stent 12 along one or both axis. A coating composition or substance is sprayed and the spraying is terminated. This is followed by rotation of the stent 12 about one or more of the described axis. Rotation about two axis can be contemporaneous or sequential.

In one embodiment, the stent 12 is rotated during the application of the coating composition. A coating composition or substance is sprayed contemporaneously/during the rotation of the stent 12 about one or more of the described axis. For example, referring to FIG. 1, the stent 12 is sprayed with the coating composition (e.g., polymer, solvent and/or drug) while the table 16 and stent 12, along axis 20, are rotated concomitantly or, alternatively, while the table 16 and stent 12 are rotated in sequence. In some embodiments, during the application process, only the table 16 is rotated or only the stent 12, along axis 20, is rotated while the other remains stationary.

The thickness of the wet coating system before drying can be between about 5 and 500 micrometers, for example, 450 micrometers.

"Coating system" can be defined as a liquid composition which includes a polymeric material. Optionally, the coating system can also contain a therapeutic substance, an agent or a drug. The polymeric material can be dissolved in a solvent. The polymeric material can also form a colloid system, e.g., by being emulsified in a carrier such as water. The colloid system can contain between about 2 mass % and about 25 mass % of the polymeric material.

Using a motor, the table 16 can then be rotated about the axis 22. The speed of rotation of the table 16 can be between about 300 revolutions per minute (rpm) and about 10,000 rpm, for example, about 4,000 rpm. The stent 12 can also be optionally rotated about the longitudinal axis 20 at a stent speed. The stent speed can be between about 100 rpm and about 5,000 rpm, for example, about 1,000 rpm.

Figure 4:
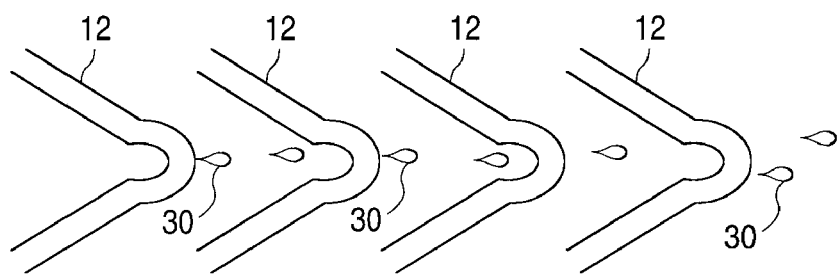
FIG. 4 illustrates a close-up view of a stent during the process of coating using the apparatus according to an embodiment of the present invention.

When the table 16 is rotated, the wet coating system on the stent 12 flows along the surface of the stent 12 and the excess wet coating 30 is discharged by the centrifugal force (FIG. 4), until a desired coating thickness is reached. Typically all of the solvent or colloid system carrier present in the wet coating system can be evaporated, and only trace amounts of the solvent or carrier may remain. As a result, an essentially dry coating is solidified on the stent. The remainder of the solvent or the carrier can be subsequently removed by drying the coating at an elevated temperature. The drying can be conducted under a vacuum condition.

The desired thickness of the resulting coating can be estimated according to the equation (I):

$$T = V_p (3\mu/4\rho\omega^2 t)^{1/2} \tag{I}$$

where T is the coating thickness;
$V_p$ is the volume fraction of polymer in the coating;
$\mu$ is the viscosity of the coating;
$\rho$ is the density of the coating;
$\omega$ is the angular velocity of rotation of the table 16; and
t is the time for which the table 16 is rotated.

Accordingly, to reach the desired thickness of the dry coating, those having ordinary skill in the art can first formulate the desired wet coating system. The wet coating system will have fixed values of $V_p$, $\mu$, and $\rho$. Then, $\omega$ and t can be selected, depending on what value of T is desired.

The value of thickness T estimated according to the equation (I) is only approximate, because equation (I) presumes the stent as a smooth cylinder and does not take into account variables such as solvent evaporation, gravitational effects, or rotation of the stent 12 about the longitudinal axis 20. For example, rotating the stent 12 about the axis 20 can increase the rate of airflow around the stent 12, thereby increasing the evaporation rate of the solvent which, in turn, speeds solidification of the coating. Therefore, the value of thickness that can be achieved in the same time period can be higher than the value calculated according to the equation (I).

Representative examples of polymers that can be used in the coating system include poly(ethylene-co-vinyl alcohol) (EVAL), poly(hydroxyvalerate), poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyphosphoester, polyphosphoester urethane, poly(amino acids), polyacetals, cyanoacrylates, poly(trimethylene carbonate), poly(iminocarbonate), co-poly(ether-esters) (e.g. PEO/PLA), polyalkylene oxalates, polyphosphazenes, biomolecules (such as fibrin, fibrinogen, cellulose, starch, collagen and hyaluronic acid), polyurethanes (such as CORETHANE available from Pfizer Corp. of New York or ELASTEON available from AorTech Biomaterials Co. of Chatswood, Australia), silicones, polyesters, polyolefins, polyisobutylene and ethylene-alphaolefin copolymers, acrylic polymers and copolymers (such as poly(butyl methacrylate), poly(ethyl methacrylate) or poly(hydroxyethyl methacrylate)), vinyl halide polymers and copolymers (such as polyvinyl chloride), polyvinyl ethers other than polyacetals, polyvinylidene halides (such as polyvinylidene fluoride and polyvinylidene chloride), polyacrylonitrile, polyvinyl ketones, polyvinyl aromatics (such as polystyrene), polyvinyl esters (such as polyvinyl acetate, acrylonitrile-styrene copolymers, ABS resins, and ethylene-vinyl acetate copolymers), polyamides (such as Nylon 66 and polycaprolactam), alkyd resins, polycarbonates, polyoxymethylenes, polyimides, polyethers, epoxy resins, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

Examples of suitable solvents include, but are not limited to, dimethylsulfoxide (DMSO), chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, isopropanol admixed with water, N-methylpyrrolidinone, toluene, and combinations thereof.

The drug can include any substance capable of exerting a therapeutic or prophylactic effect for a patient. The drug may include small molecule drugs, peptides, proteins, oligonucleotides, and the like. The drug could be designed, for example, to inhibit the activity of vascular smooth muscle cells. It can be directed at inhibiting abnormal or inappropriate migration and/or proliferation of smooth muscle cells to inhibit restenosis.

Examples of drugs include antiproliferative substances such as actinomycin D, or derivatives and analogs thereof (manufactured by Sigma-Aldrich of Milwaukee, Wis., or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, tacrolimus, dexamethasone, and rapamycin and structural derivatives or functional analogs thereof, such as 40-O-(2-hydroxy)ethyl-rapamycin (known by the trade name of EVEROLIMUS available from Novartis), 40-O-(3-hydroxy)propyl-rapamycin, 40-O-[2-(2-hydroxy)ethoxy]ethyl-rapamycin, and 40-O-tetrazole-rapamycin.

The apparatus and method of the present invention have been described in conjunction with a stent. However, the apparatus and method can also be used with a variety of other medical devices. Examples of the implantable medical device, that can be used in conjunction with the embodiments of this invention include stent-grafts and grafts. The underlying structure or scaffolding design of the device can be of virtually any design. The device can be made of a metallic material or an alloy such as, but not limited to, cobalt-chromium alloys (e.g., ELGILOY), stainless steel (316L), "MP35N," "MP20N," ELASTINITE (Nitinol), tantalum, tantalum-based alloys, nickel-titanium alloy, platinum, platinum-based alloys such as, e.g., platinum-iridium alloy, iridium, gold, magnesium, titanium, titanium-based alloys, zirconium-based alloys, or combinations thereof. Devices made from bioabsorbable or biostable polymers can also be used with the embodiments of the present invention.

"MP35N" and "MP20N" are trade names for alloys of cobalt, nickel, chromium and molybdenum available from Standard Press Steel Co. of Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

Some embodiments of the present invention can be further illustrated by the following Examples.

Example 1

A 13 mm PENTA stent (available from Guidant Corp.) can be placed on a mandrel and the mandrel can be mounted onto a coating apparatus as shown by FIG. 1.

A first composition can be prepared, comprising:
(a) about 4 mass % of EVAL; and
(b) the balance, a solvent blend, the blend comprising about 80 mass % of dimethylacetamide (DMAC) and about 20 mass % of pentane.

With the table stationary, the EVAL composition can be applied in a drop-wise manner to the stent to form a primer layer. A sufficient amount of the EVAL solution can be added to ensure the entire stent is wetted. Immediately after application of the EVAL composition, the table can be accelerated to a speed of about 8,000 rpm at a ramp rate of about 8,000 rpm/s (about 133.3 r/s$^2$). The term "ramp rate" is defined as the acceleration rate of the spinner. The ramp rate of 8,000 rpm/s means that in 1 second the spinner would accelerate to 8,000 rpm from a standstill.

The table speed of about 8,000 rpm can be held for about 8 seconds and then the table can be decelerated at a ramp rate of about 4,000 rpm/s until the table comes to a complete stop. This means that the table speed is reduced from about 8,000 rpm to 0 within about 2 seconds. Residual solvent can be removed by baking the stent at about 140° C. for about 1 hour.

Next, the stent can be reinstalled in the same spinning apparatus. A second composition can be prepared, comprising:
(c) about 6 mass % of poly(butyl methacrylate);
(d) about 3 mass % of 17-β-estradiol; and
(e) the balance, a solvent blend, the blend comprising about 60 mass % of acetone and about 40 mass % of xylene.

With the table stationary, the second composition can be applied in a drop-wise manner to the stent to form a drug-polymer layer. Application of the drug in a drop-wise manner mitigates the safety requirements that are needed as compared to the precautions that are taken during the handling of atomized pharmaceuticals. A sufficient amount of the second solution can be added to ensure the entire stent is wetted. Immediately after the second composition has been applied, the table can be accelerated at a rate of about 4,000 rpm/s to a speed of about 4,000 rpm, held for about 9 seconds, and then decelerated at a rate of about 4,000 rpm/s until the table comes to a complete stop. The stent can be baked at about 80° C. for about 30 minutes to remove residual solvent.

Example 2

A 13 mm PENTA stent can be mounted on a mandrel and the mandrel can be mounted onto an apparatus as shown in FIG. 2. The mandrel can be mounted in such a way that the mandrel is free spinning. For example, the mandrel can be attached to the arms using bearings located on the arms. As the table turns, the mandrel spins due to greater air friction on the top surfaces of the stent than the bottom surfaces. The offset distance can be about 50 mm, and the counterweight can weigh between about 10 grams and about 100 grams, for example, about 32 grams.

A first composition can be prepared, comprising:
(a) about 4 mass % of poly(butyl methacrylate); and
(b) the balance, a solvent blend, the blend comprising about 60 mass % of acetone and about 40 mass % of xylene.

With the table stationary, the first composition can be applied in a drop-wise manner to the stent for forming a primer layer. A sufficient amount of the poly(butyl methacrylate) solution can be added to ensure the entire stent is wetted. Immediately after application of the first composition, the stent can be accelerated to a speed of about 4,000 rpm at a ramp rate of about 8,000 rpm/s. The 4,000 rpm speed can be held for about 8 seconds and then decelerated at a rate of about 4,000 rpm/s. Residual solvent can be removed by baking the stent at about 80° C. for about 1 hour.

Next, the stent can be reinstalled in the same spinning apparatus. A second composition can be prepared, comprising:
(c) about 2 mass % of poly(butyl methacrylate);
(d) about 1.6 mass % of EVEROLIMUS; and
(e) the balance, a solvent blend, the blend comprising about 60 mass % of acetone and about 40 mass % of xylene.

With the table stationary, the second composition can be applied in a drop-wise manner to the stent to form a drug-polymer layer. A sufficient amount of the second solution can be added to ensure the entire stent is wetted. Immediately after the second composition has been applied, the table can be accelerated at a rate of about 2,000 rpm/s to a speed of about 4,000 rpm, held for about 9 seconds, and then decelerated at a rate of about 4,000 rpm/s until the table comes to a complete stop. The stent can be baked at about 80° C. for about 30 minutes to remove residual solvent.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of coating a stent, comprising conducting the following acts at the same time:
applying a coating substance to the stent;
rotating the stent about a first axis of rotation; and
rotating the stent about a second axis of rotation,
wherein the first axis of rotation intersects the second axis of rotation at an angle.

2. The method of claim 1, wherein the first axis of rotation is perpendicular to the second axis of rotation.

3. The method of claim 1, wherein the first axis of rotation intersects a center of the mass of the stent and the second axis of rotation is along a longitudinal central axis of the stent.

4. The method of claim 1, wherein the first axis of rotation intersects a part of the body of the stent and the second axis of rotation is along a longitudinal central axis of the stent.

5. The method of claim 1, wherein the first axis of rotation intersects a center of the mass of the stent, the second axis of rotation is along a longitudinal central axis of the stent, and the first axis of rotation is perpendicular to the second axis of rotation.

6. The method of claim 1, wherein the stent is positioned off-set, at a distance away from the first axis of rotation.

7. The method of claim 1, wherein the first axis of rotation is perpendicular to a longitudinal axis of the stent.

8. A method of coating a stent, comprising conducting the following acts at the same time:
applying a coating substance to the stent;
rotating the stent about a first axis of rotation; and
rotating the stent about a second axis of rotation, wherein the first axis of rotation is not parallel and not perpendicular to the second axis of rotation.

9. The method of claim 1, wherein the first axis of rotation intersects a center of the mass of the stent and the second axis of rotation is along a longitudinal central axis of the stent.

10. The method of claim 1, wherein the first axis of rotation intersects a part of the body of the stent and the second axis of rotation is along a longitudinal central axis of the stent.

11. The method of claim 1, wherein the stent is positioned off-set, at a distance away from the first axis of rotation.

12. The method of claim 1, wherein the first axis of rotation intersects the second axis of rotation at an angle.

* * * * *